United States Patent
Herskowitz et al.

(10) Patent No.: US 7,276,629 B2
(45) Date of Patent: Oct. 2, 2007

(54) HYDROGENATION OF IMINE INTERMEDIATES OF SERTRALINE WITH CATALYSTS

(75) Inventors: Mordechay Herskowitz, Meitar (IL); Mark Kaliya, Beer-Sheva (IL)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 0 days.

(21) Appl. No.: 10/825,386

(22) Filed: Apr. 14, 2004

(65) Prior Publication Data

US 2005/0085669 A1    Apr. 21, 2005

Related U.S. Application Data

(60) Provisional application No. 60/462,816, filed on Apr. 14, 2003.

(51) Int. Cl.
*C07C 209/52* (2006.01)
(52) U.S. Cl. .................................... 564/308
(58) Field of Classification Search .................. None
See application file for complete search history.

(56) References Cited

U.S. PATENT DOCUMENTS

| | | | |
|---|---|---|---|
| 2,486,361 A * | 10/1949 | Nahin et al. | 208/137 |
| 3,860,532 A * | 1/1975 | Takase et al. | 502/235 |
| 4,536,518 A | 8/1985 | Welch, Jr. et al. | |
| 6,034,274 A * | 3/2000 | Vukics et al. | 564/308 |
| 6,232,501 B1 * | 5/2001 | Steiner et al. | 564/308 |
| 6,593,496 B1 | 7/2003 | Quallich et al. | |
| 2003/0105364 A1 | 6/2003 | Berger et al. | |
| 2003/0166970 A1 | 9/2003 | Mendelovici et al. | |

FOREIGN PATENT DOCUMENTS

| EP | 1059287 | 12/2000 |
|---|---|---|
| WO | WO98/27050 | 6/1998 |
| WO | WO99/47486 | 9/1999 |
| WO | WO99/57093 | 11/1999 |
| WO | WO 01/09080 | 2/2001 |
| WO | WO 01/16089 | 3/2001 |
| WO | WO 01/30742 | 5/2001 |
| WO | WO 01/49638 | 7/2001 |
| WO | WO 01/68566 | 9/2001 |
| WO | WO 02/102761 | 12/2002 |

OTHER PUBLICATIONS

Rathousky et al., Applied Catalysis A: General, 79 (1991), pp. 167-180.*
The Merck Index, 12th edition (1996), Budavari ed., Merck & Co. Inc., Whitehouse Station, NJ, entry No. 8612.*

* cited by examiner

*Primary Examiner*—Brian Davis
(74) *Attorney, Agent, or Firm*—Kenyon & Kenyon LLP

(57) ABSTRACT

Provided are hydrogenation processes of sertraline imine intermediates with catalysts in various reactors.

46 Claims, No Drawings

HYDROGENATION OF IMINE INTERMEDIATES OF SERTRALINE WITH CATALYSTS

RELATED APPLICATIONS

This application claims the benefit of U.S. Provisional Patent Application Ser. No. 60/462,816, filed Apr. 14, 2003, which is incorporated herein by reference.

FIELD OF INVENTION

The present invention relates to hydrogenation methods for preparation of sertraline.

BACKGROUND OF INVENTION

Sertraline hydrochloride, (1S-cis)-4-(3,4 dichlorophenyl)-1,2,3,4-tetrahydro-N-methyl-1-naphthalenamine hydrochloride, having the formula:

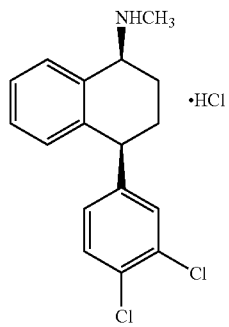

is approved, under the trademark Zoloft®, by the U.S. Food and Drug Administration, as a serotonin re-uptake inhibitor for the treatment of depression, obsessive-compulsive disorder, panic disorder and post-traumatic disorder. Only cis sertraline is therapeutically active.

U.S. Pat. No. 4,536,518 describes a synthesis of sertraline hydrochloride from sertralone having the following formula:

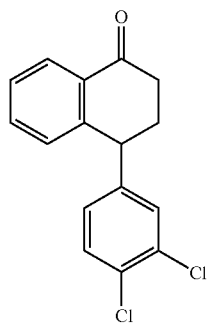

The process for synthesizing sertraline from sertralone has two steps. First, sertralone is condensed with methyl amine in the presence of an acid catalyst, to yield the Schiff base of sertralone, "sertraline-1-imine":

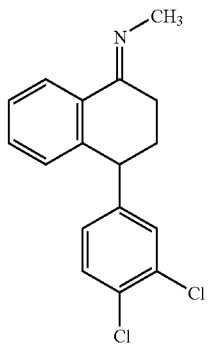

The imine is then reduced to sertraline. The reduction process of U.S. Pat. No. 4,536,518 involves the hydrogenation of sertraline-1-imine concentrate at room temperature for two hours over 10% Pd/C catalyst in an atmosphere of hydrogen (1 atm pressure). The product is a racemic mixture of the cis and trans diastereoisomers ("(±)-cis/trans-sertraline") in the ratio of approximately 3 to 1. The '518 patent discloses that reduction with NaBH$_4$ gives a cis:trans ratio of about 1:1.

Two publications, WO 01/30742 and WO 98/27050, disclose the stereoselective reduction of sertraline-imine derivatives. The publication, WO 01/30742, discloses replacing the methyl group of sertraline 1-imine with an optionally substituted bulky benzyl group to increase the cis to trans ratio during hydrogenation, followed by additional steps of converting the bulky group to a methyl group. Additionally, the publication, WO 01/30742, discloses: "The reduction may be performed using complex hydrides (e.g. NaBH$_4$) or by hydrogenation. Reduction performed by catalytic hydrogenation tends to give better selectivity that reduction using the complex hydrides. For example, aliquots of N-[4-(3,4 dichlorophenyl)-3,4-dihydro-1(2H)-naphthalenylidene]-benzylamine were reduced with NaBH$_4$ and Raney nickel/H$_2$ respectively, and subsequently reductively alkylated with formaldehyde, whereafter the cis/trans ratio was analyzed. The result was a ratio of 53.8/46.2 using NaBH$_4$ compared to 82.9/17.1 for Raney nickel/H$_2$ which clearly demonstrates the selectivity for the catalytic hydrogenation. An even higher selectivity with a cis/trans ratio of 93.5/6.5 has been observed using palladium on carbon."

The publication, WO 98/27050, discloses obtaining sertraline by reducing an N-oxide derivative of the imine. In Example 1, the N-oxide derivative is hydrogenated with Raney nickel catalyst, while in Example 2 a 10% palladium on carbon is used as a catalyst. A cis product with an 81% yield is obtained in both instances. According to WO 98/27050, the N-oxide group may then be removed by addition of HCl to the N-oxide compound in ethanol.

The publication, WO 01/16089, discloses a process of reductive amination of sertralone to cis and trans sertraline. In Example 1, sertralone is reduced in the presence of Raney nickel and methylamine. The yield provided in Example 1 is 48–51% of the cis isomer.

The publication, WO 99/57093, discloses a process of selective hydrogenation with a palladium catalyst pretreated with an alkyl halide. The publication discloses that the process of the '518 patent may lead to 10% of dechlorinated side products, while the process of the publication has a "total amount of said contaminated by-products . . . below 0.5%." In regards to the cis/trans ratio, the ratio provided is 85–95% in the description of the invention. Alkyl halides however are problematic for use on an industrial scale since halogenated reagents are often not environmentally friendly.

U.S. Pat. No. 6,593,496 discloses preparing sertraline-I imine by reacting sertralone with monomethylamine and either titanium tetrachloride or molecular sieves. The hydrogenation illustrated in scheme 1 is carried out with a palladium catalyst in THF.

In US 2003/0105364, a process is provided for obtaining optically pure sertralone through chromatography. The examples do not illustrate hydrogenation.

In US 2003/0166970, a process for making (±)-sertraline with a cis/trans ratio of greater than about 3:1 is provided by hydrogenation of sertraline-1-imine at a temperature of at least about 40° C. using a palladium or a platinum catalyst.

There is a need in the art for additional processes for hydrogenation of imines for preparation of sertraline.

SUMMARY OF THE INVENTION

In one aspect, the present invention provides a process for preparing sertraline comprising the step of hydrogenating an imine of the formula:

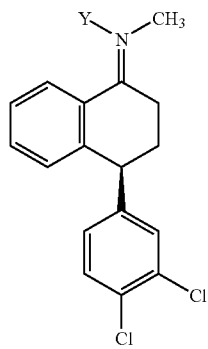

with a cobalt catalyst and converting the hydrogenated compound to sertraline if necessary, wherein Y is optionally an oxygen atom.

In another aspect, the present invention provides a process for preparing sertraline from an imine having the formula:

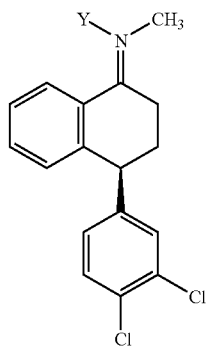

wherein Y is optionally an oxygen atom, comprising the step of hydrogenating the imine with a metal catalyst in a trickle bed reactor and converting the hydrogenated compound to sertraline if necessary.

In another aspect, the present invention provides a process for preparing sertraline from an imine having the formula:

wherein Y is optionally substituted with an oxygen atom, comprising the step of hydrogenating the imine with a nickel containing catalyst having fixed support in a batch reactor and converting the hydrogenated compound to sertraline if necessary.

In another aspect, the present invention provides a process for preparing sertraline from sertraline-1-imine comprising the step of reducing sertraline-1-iminine in a batch reactor with a Ni/SiO$_2$ catalyst.

In another aspect, the present invention provides a process for preparing sertraline from sertraline-1-imine comprising the step of hydrogenating sertraline-1-imine in the presence of a catalyst in a trickle bed reactor.

In another aspect, the present invention provides a process for preparing sertraline by providing a cobalt containing catalyst made up of cobalt fixed on an alumina-silica support, loading the catalyst in a trickel bed reactor, reducing the cobalt catalyst to an oxidation state of CoO, feeding the reactor with hydrogen and a solution of sertraline 1-imine in THF, recovering the sertraline and optionally converting the sertraline to sertraline hydrochloride.

In another aspect, the present invention provides a process for preparing sertraline comprising hydrogenating sertraline-1-imine with a cobalt catalyst in a trickle-bed reactor fed with sertraline imine solution in THF of 30 g imine/L at weight hourly space velocity of about 12.5 $h^{-1}$, a pressure of about 8 bar and a temperature of about 120° C.

In another aspect, the present invention provides a process for preparing sertraline comprising hydrogenating sertraline-1-imine in solution in THF having a concentration in the range of about 10 to about 140 g/L with a nickel catalyst fixed on a support in a trickle-bed reactor, at a temperature of about 65 to about 150° C., a pressure of about 2 to about 15 bar, a WHSV of about 40 to about 120 per hour, and a hydrogen feeding range of about 50 to about 2000 per hour.

In another aspect, the present invention provides a process for preparing sertraline comprising hydrogenating with a nickel catalyst fixed on a support in a batch reactor sertraline-1-imine in solution in THF having a concentration in the range of about 30 to about 125 g/L, pressure of about 5 to about 8 bar, temperature range of about 65 to about 150° C.

In another aspect, the present invention provides sertraline or a hydrochloride salt thereof in solid state comprising less than about 0.1% of the dechlorinated side products as area percentage HPLC according to U.S. Pharmacopoeia, and their pharmaceutical compositions.

In another aspect, the present invention provides a process for preparing a cobalt catalyst suitable for reduction of sertraline-1-imine by calcining an alumina-silica support, evaporating moisture from the calcined support, contacting the calcined support with an aqueous solution of cobalt nitrate to saturate the surface of the support to obtain a catalyst, drying the catalyst and calcining the catalyst in the presence of hydrogen to obtain an oxidation state of CoO.

DETAILED DESCRIPTION OF THE INVENTION

As used herein, the term dechlorinated side (DCS) compounds refers to sertraline which is missing at least one of the chlorines on the phenyl group. DCS-1 refers to the chlorine in the para position missing, and DCS-2, the chlorine in the meta position. DCS-3 refers to the impurity without any chlorine atom; its level is usually undetected unless the reaction is not carefully controlled. If the level of DCS-1 is more than 1%, DCS-3 is also detected.

As used herein, the term calcine refers to heating to a high temperature but below the melting point, causing at least one of loss of moisture, reduction or oxidation, and decomposition of various compounds. A suitable temperature is above about 450° C., most preferably about 500° C. Calcination of cobalt nitrate proceeds as following:

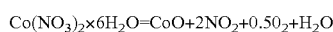

$$Co(NO_3)_2 \times 6H_2O = CoO + 2NO_2 + 0.5O_2 + H_2O$$

Space velocity is calculated as follows: the mass/volume of feed per unit of catalyst per unit of time (e.g. WHSV=weight hourly space velocity=x kg-feed/kg-catalyst/hour). GHSV, gas hourly space velocity is calculated as=v nL $H_2$ feed/L catalyst/hour.

The present invention provides for hydrogenation of an imine with a nickel or a cobalt containing catalyst to obtain sertraline. The following catalysts may be used:

| Catalyst | Type | Promoters |
|---|---|---|
| Ni, G-69 (Sud-Chemie) | Ni/Kieselguhr | Zr |
| Ni, (G-49 (Sud-Chemie) | Ni/Kieselguhr | — |
| Pd ((Johnson Matthey) (Trickel-bed reactor) | Pd/C | — |
| Pd ((Johnson Matthey) (Trickel-bed reactor) | Pd/$Al_2O_3$ | — |
| Co, T-4424 (Sud-Chemie) | Co/proprietary support | Mn, Mg |
| Co, T-44o5(Sud-Chemie) | Co/$SiO_2$—$Al_2O_3$ | — |
| Co, G-62 (Sud-Chemie) | Co/$SiO_2$—$Al_2O_3$ | Ca |
| TSCo-1 (BGU) | 28% Co/$_\gamma$-$Al_2O_3$ | — |
| TSCo-3(BGU) | 23% Co/$SiO_2$ | — |
| TSCo-4(BGU) | 25% Co/SA 3135 | — |
| TSCo-5 (BGU) | 15% Co/SA 3135 | — |
| TSCo-6 (BGU) | 15% Co/SA 3132 | — |

Pd/C was also used in trickle bed reactor, but the selectivity to cis sertraline was not as good as that with cobalt (Table A).

TABLE A

Performance of Pd catalysts in trickle-bed reactor

| Catalyst | Temp °C. | Feed rate g/h | Imine Conv, % | Cis-sertraline % | Sertralone % | Total DCS, % |
|---|---|---|---|---|---|---|
| 0.8% Pd/C | 40 | 25 | 90 | 60 | 2 | 2 |
| 5% Pd/$Al_2O_3$ | 40 | 80 | 70 | 63 | 0.6 | 1 |

The imine used to obtain sertraline preferably has the following structure:

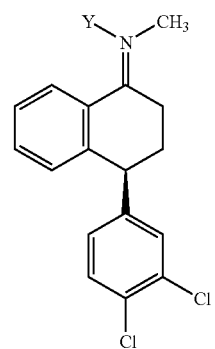

wherein in the most preferred embodiment Y is not substituted, i.e., sertraline-1-imine. In another embodiment, Y is an oxygen atom, thus providing the N-oxide compound disclosed in the publication WO 98/27050.Sertraline-1-imine is used as a starting material in the illustrations of the present invention. The starting material may be racemic or a pure enantiomer of sertraline-1-imine, i.e. at least about 90% pure, more preferably 95% pure. Such purity may be determined for example by a chiral HPLC column, or rotation of light.

In one embodiment, an imine is hydrogenated with a commercial nickel catalyst in a trickle-bed reactor. The nickel catalyst used may for example be G-69, G-49 or G-96, supplied by Sud-Chemie (Munich, Germany).

The nickel catalyst preferably has a surface area of about 50 to about 200, with about 150 m$^2$/g being more preferred. The density of the nickel catalyst is preferably from about 0.8 to about 1.5, with about 1.1 Kg/L being more preferred. The granule size of the catalyst is preferably about 0.7 to about 5, with about 1 mm being more preferred. The amount of nickel deposited on the support is preferably about 30 to about 80, with about 45 (wt/wt) being more preferred.

With a trickle-bed, or another kind of a fixed bed reactor, the conditions used are preferably as follows:

A temperature of from about 65 to about 150, with about 90° C. being preferred.

A pressure of from about 2 to about 20, with about 8–10 bar being preferred.

An imine solution in THF having a concentration in the range of from about 10 to about 140, with about 30 g/L being preferred. Other solvents include methanol, ethanol, 1,4 dioxane, toluene and ethyl acetate.

A WHSV of from about 40 to about 120, with about 85 per hour being preferred.

A hydrogen feeding range of about 50 to about 2000 per hour.

In a preferred embodiment, the commercial catalyst G-69, supplied by Sud-Chemie (Munich, Germany), is used under the following preferred conditions:

a trickle-bed reactor fed with sertraline-imine in tetrahydrofuran ("THF") at WHSV 77 h$^{-1}$;

pressure of from about 8 to about 10 bar;

temperature of about 90° C.; and granules of the catalyst of from about 30 to about 50 mesh and of about 50 to about 80 mesh.

The selectivity of cis and trans for this embodiment is preferably about 86% and about 12% respectively. The cis/trans ratio is preferably about 7.2:1, DCS-compounds content is preferably about 0.1% and the conversion is preferably complete.

In another embodiment, hydrogenation with a nickel containing catalyst on fixed support is carried out in a batch type reactor with a nickel catalyst. The following preferred reaction conditions may be used for the hydrogenation process:

The reaction solvent: methanol, ethanol, toluene, ethylacetate, 1,4-dioxane and THF, with 1,4-dioxane and THF being more preferred;

A reaction pressure of from about 5 to about 8 bar, with about 8 bar being preferred;

A temperature range of from about 65 to about 150° C., with from about 120 to about 150° C. being more preferred; and An imine loading range of from about 30 to about 125 g/L, more preferably compared to THF.

The summary of the various runs with a batch type reactor is disclosed in Tables 1–4. Table 1 illustrates the high conversion rate obtained from the G-69 catalyst, which is an Ni/Kieselguhr catalyst used with a Zr promoter. Table 2 illustrates the high conversion rate and low amounts of DCS obtained with THF as a solvent. Table 3 illustrates an increase in yield with increase in temperature. Table 4 illustrates an increase in yield with increase in pressure.

TABLE 1

Hydrogenation with Ni containing catalysts with a batch reactor:

| Catalyst | T (C.) | P (bar) | Catalyst Loading, g/l | Solvent | Cis-SRT | DCS-Compounds (% area HPLC) | Sertralone (% area HPLC) | Conversion |
|---|---|---|---|---|---|---|---|---|
| G-69 | 65 | 5 | 4.7 | MeOH | 79.8 | 1.1 | 2 | 100 |
| G-49 | 100 | 5 | 4.7 | MeOH | 68 | 0.1 | 2.5 | 69 |
| G-96 | 65 | 5 | 4.7 | MeOH | 11 | 0.3 | 14.1 | 29.5 |
| Ni-5249 | 70 | 5 | 3.1 | MeOH | 78.7 | 0.9 | 3 | 70 |

TABLE 2

Hydrogenation with catalyst G-69 in various solvents with a batch reactor:

| Solvent | Press., bar | Temp., ° C. | Conversion (%) | Cis-Sertraline (%) | DCS-compounds (% area HPLC) | Sertralone (% area HPLC) |
|---|---|---|---|---|---|---|
| MeOH | 5 | 85 | 100 | 79.9 | 1.2 | 2 |
| EtOH | 5 | 85 | 100 | 74.6 | 2.8 | 1 |
| Toluene | 5 | 120 | 93 | 69.1 | 0.1 | 6.9 |
| EtOAc | 5 | 120 | 70 | 78.7 | 0.9 | 3 |
| 1,4-dioxane | 5 | 120 | 93.7 | 81.6 | 0.04 | 6.2 |
| THF | 8 | 120 | 99 | 83.4 | 0.02 | 1.4 |

The catalyst loading was 4.7 g/l

TABLE 3

The results of the hydrogenation in THF with catalyst
G-69 in a batch reactor:

| Temperature (° C.) | Press., bar | Cis-Sertraline (%) | DCS-Compounds (% area HPLC) | Sertralone (% area HPLC) |
|---|---|---|---|---|
| 65 | 5 | 79.2 | 0.08 | 3 |
| 95 | 5 | 81.1 | 0.21 | 2.1 |
| 120 | 8 | 82.3 | 0.24 | 1.5 |
| 150 | 9 | 83.7 | 0.3 | 2.1 |

TABLE 4

The effect of the pressure to the reaction with catalyst G-69
in THF in a batch reactor:

| Temp. (° C.) | Press., bar | Conversion (%) | Cis-Sertraline (%) | DCS-Compounds (% area HPLC) | Sertralone (% area HPLC) |
|---|---|---|---|---|---|
| 90 | 3 | 98.8 | 77.6 | 0.17 | 3 |
| 90 | 8 | 99 | 80.3 | 0.05 | 1.4 |

In another embodiment, a commercially available cobalt containing catalyst or one as prepared in Examples 1–4 ("proprietary") is used. The cobalt commercial catalyst (G-62 supplied by Sud-Chemie) affords a cis:trans ratio of about 11.8:1, and an amount of DCS-compounds of about <0.1%.

The cobalt catalyst may be prepared as illustrated in Examples 1–4. Granules of alumina-silica support are impregnated by a solution of cobalt. The cobalt becomes fixed on the support. The cobalt catalyst is then activated by being reduced with hydrogen to obtain an oxidation state of CoO.

For example, the proprietary cobalt catalyst may be prepared by calcining an alumina-silica support, evaporating moisture from the calcined support, contacting the calcined support with an aqueous solution of cobalt nitrate to saturate the surface of granules of the support to obtain a catalyst, drying the catalyst and calcining the catalyst in the presence of hydrogen to obtain an oxidation state of CoO. Preferably, calcining is carried out by heating to a temperature of at least about 450° C., more preferably to a temperature of about 500° C. Preferably, the evaporating is carried out under reduced pressure, more preferably at less than about 100 mmHg, and most preferably less than about 50 mmHg. The drying is preferably carried out of about 90° C. to about 150° C., more preferably at a temperature is about 120° C.

The GHSV for the catalyst reduction is preferably from about 2000 to about 2500 per hour, more preferably about 2500 h$^{-1}$. Preferably, the temperature during reducing is increased (preferably from about room temperature) to at least about 450° C., more preferably to about 500° C., at interval of about 3–8° C./min, more preferably about 5° C./min, and maintained constant for at least about 2 hours, more preferably of about 2 hours to about 10 hours, and most preferably for about 4 hours.

The cobalt catalyst may be reactivated by removal of tar deposited on the catalyst surface. After tar removal, the catalyst may be reduced again if its oxidation state has substantially increased.

The proprietary cobalt catalyst (TSCo-3, TSCo-4 and TSCo-5) allows reaching a cis:trans ratio of about 5.7:1 to 13.8:1, about <0.1% DCS-compounds, and at an imine conversion rate of from about 80 to about 100%. The performance of the proprietary cobalt catalyst may be influenced by use of an optimal support, preferably alumina-silica, optimal content of cobalt oxide deposited on the support, and methods of catalyst preparation and activation as disclosed in Examples 1–4.

The cobalt catalyst preferably has a surface area of from about 6 to about 100, with about 10 m$^2$/g being more preferred. The pore diameter range of the cobalt catalyst is preferably from about 100 to about 300, with about 180 angstroms being more preferred. The bulk density of the cobalt catalyst is preferably from about 0.7 to about 1.2, with about 0.8 being preferred. The granule size of the catalyst is preferably from about 0.1 to about 3.5, with about 1 mm being preferred. The amount of cobalt deposited on the support is preferably from about 10 to about 25, with about 15 (wt/wt) being preferred.

The cobalt catalyst packed in a column is then fed hydrogen and an imine solution. Preferably the solvent used for the imine solution is THF. Other preferred solvents include methanol and 1,4 dioxane. The concentration of the imine solution is preferably from about 10 to about 120, with about 30 gram/L being more preferred. The weight hourly space velocity is preferably from about 5 to about 15, with about 10 per hour being more preferred. Hydrogen is preferably fed at a rate of from about 25 to about 5000, with about 3300 per hour being more preferred. The temperature is preferably from about 80 to about 150, with about 130° C. being more preferred. The pressure is preferably from about 5 to about 20, with about 8 bar being more preferred.

The proprietary cobalt catalyst works optimally under the following preferred conditions: a trickle-bed reactor fed with sertraline imine solution in THF (30 g imine/L) at weight hourly space velocity ("WHSV") about 12.5 h$^{-1}$, pressure of about 8 bar and a temperature of about 120° C.

After hydrogenation, separation of the desirable cis isomer from the undesirable cis and anti isomer if needed may be carried out by selective precipitation with mandeleic acid, as disclosed in Example 5. (±)-cis/trans-Sertraline hydrochloride may also be recrystallized once and dissolved in an appropriate organic solvent, such as ethanol, isopropanol, methanol, n-butanol, and iso-butanol. Ethanol is preferred. The optical resolution is performed by adding solid base, e.g., potassium hydroxide, sodium hydroxide, sodium carbonate (Na$_2$CO3) and sodium bicarbonate (NaHCO$_3$), directly to the sertraline hydrochloride racemate solution. The salts, are then removed by an appropriate method, e.g., by filtration. The optically active, selective precipitant, as described above, e.g., (D)-mandelic acid, is added to the organic solution and the (+)-cis-sertraline-precipitant, e.g., (+)-cis-sertraline-mandelate, is precipitated directly from this organic solution. The resulting crude (+)-cis-sertraline-precipitant is recrystallized. The recrystallized (+)-cis-sertraline-precipitant, e.g.,(+)-cis-sertraline-mandelate, is dissolved in organic solvent and the mandelic acid is removed with base, such as, by washing the organic solution with aqueous basic solutions, e.g., 10–20% sodium hydroxide (NaOH) solution, or 10–20% potassium (KOH) solution. The (+)-cis-sertraline free base is isolated, dissolved in an appropriate organic solvent, and is treated with hydrochloric acid. (+)-cis-Sertraline hydrochloride is precipitated as crystals and dried to give (+)-cis-sertraline hydrochloride Form V.

In addition to Form V, the sertraline may be crystallized as various polymorphic forms of sertraline hydrochloride as disclosed in U.S. Pat. Nos. 6,500,987, 6,495,721 and 6,452, 054, incorporated herein by reference. In one embodiment sertraline hydrochloride Form II is prepared by bubbling HCl gas through a solution of sertraline in n-butanol.

Pharmaceutical compositions of the present invention contain sertraline hydrochloride containing less than about 0.1%, more preferably less than about 0.5%, of the dechlorinated side products as area percentage HPLC according to U.S. Pharmacopoeia. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants may be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which may cause the product to have pitting and other surface irregularities. A lubricant may be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, sertraline hydrochloride and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Preferably, the pharmaceutical formulations of the present invention are solid dosage forms in the form of a tablet for the oral administration of sertraline hydrochloride. The highly pure sertraline hydrochloride used for preparing a tablet may be in the form of fine crystals. Preferably, the fine crystals have a particle size distribution such that 100% of the particles are below 200 microns, more preferably below 100 microns and most preferably below about 50 microns.

EXAMPLE 1

Preparation of the Proprietary Cobalt Catalyst

The catalyst was prepared using the incipient wetness impregnation of alumina-silica. The support precursor catalyst reduction purchased from Saint-Gobain NorPro (Stow, Ohio) was first calcined at 500° C. for 12 hours before impregnation. Characteristics of the support SA3 135 is given in Table 5. Calcined SA-3 135 (5 grams), granules 1–1.2 mm, was charged into glass flask and evaporated at P=0.02 bar and 25° C. over 1 hour. An aqueous solution of cobalt nitrate (4.0 ml) containing 4.36 g of $Co(NO_3)_2 \times 6H_2O$ (98%), purchased from Aldrich (Milwaukee, Wis.), was added dropwise so that surface of all the granules was saturated by the salt solution. The catalyst was dried at 120° C. for 4 hours and calcined at 500° C. for 4 hours.

The Energy Dispersive X-Ray ("EDX") analysis indicated the contents of Co, Al, Si, 0: 15.0, 35.8, 13.8 and 35.4% wt., respectively. The XRD patterns of the material were evident for the existence of the phase $Co_3O_4$: (peaks at 2θ:18.96, 31.24, 36.68, 38,78, 44.75, 57.55). The average crystal size of CoO estimated in XRD study was 50 nm. The catalyst had surface area 11 $m^2/g$, with an average pore diameter 183 angstroms.

The catalyst (2.3 g) was loaded into a tubular stainless steal reactor (6 mm ID and 150 mm length). In the stream of hydrogen at GHSV (gas hour space velocity) 2500 $h^{-1}$, the temperature was gradually ramped to 500° C., (5° C./min), and then the temperature was maintained constant at 500° C. for 4 hours. The operating conditions of catalyst reduction were selected over Temperature Programmed Reduction ("TPR") studies carried out in AMI-100 Catalyst Characterization System from Zeton-Altamira (Pittsburgh, Pa.).

The XRD analysis of the reduced catalysts indicates the existence of the phase Co and CoO (peaks at 2θ: 36.8, 42.47, 61.41, 73.69). After the completion of the catalyst reduction, the temperature in the reactor was decreased to 120° C., and the total pressure of hydrogen was increased to 8 bar. A solution containing N-methyl-4(3,4-dichlorophenyl)-1-(-2H)-naphtalenimine (Imine) in tetrahydrofuran (THF), purchased from BioLab (99.5%), having a concentration of 30 g/L was then fed with hydrogen to the reactor. The rate of the solution feed was 25 g/h and the rate of hydrogen feed was 150 ml/mm.

(The products were analyzed by GC HP6890 (Palo Alto, Calif.): capillary column DB-17, 30 m×0.53 mm×1μ. The initial temperature was 160° C. for 26 minutes, and then the temperature was increased at a rate of 30° C./min to 250° C.).

The results of the GC analysis under conditions mentioned above are shown in table 7, which indicates that the imine was completely hydrogenated to a mixture containing: cis-(1S,4S)-N-Methyl-(3,4-dichlorophenyl)-1,2,3,4-tetrahydro-1-naphtalenamine(cis-Sertraline) as the major component, trans-(1S,4R)-N-Methyl-4(3,4-dichlorophenyl)-1,2,3,4-.tetrahydro-1-naphtalenamine(trans-Sertraline), (1S,4S)-N-Methyl-4(3-dichlorophenyl)-1,2,3,4-tetrahydro-1-naphtalenamine(DCS-1), (1S,4S)-N-Methyl-4-(4-dichlorophenyl)-1,2,3,4-tetrahydro-1-naphtalenamine (DCS-2) and Sertralone.

The content of cis-sertraline in the product of imine hydrogenation was 91%.

TABLE 5

The characteristics of the support SA 3135

| Parameter | Value |
| --- | --- |
| Aluminum oxide, % wt | 79–81 |
| Silicon oxide, % wt | 17–19 |
| Sodium oxide, % wt | 0.2–0.4 |
| Ferric oxide, % wt | 0.3–0.5 |
| Titanium dioxide, % wt | 0.4–0.5 |
| Magnesium oxide, % wt | 0.1–0.3 |
| Potassium oxide, % wt | 0.1–0.3 |
| Surface area, $m^2/g$ | 12.5 |
| Particle density, g/cc | 1.1 |

EXAMPLE 2

A catalyst containing 11% cobalt by weight was prepared and reduced as in Example 1, but 3.2 g instead of 4.36 g of $Co(NO_3)_2 \times 6H_2O$ was used for the preparation of the aqueous solution. The hydrogenation was carried out under conditions as provided in Example 1. The content of cis-sertraline in the product of imine hydrogenation was 91%.

EXAMPLE 3

The catalyst containing 25% of cobalt by weight was prepared by carrying out the incipient wetness impregnation process twice. The first impregnation was followed by drying at 120° C. for 4 hours, and then calcination at 500° C. for 4 hours was carried out as in Example 1. S Scanning Electronic Microscopy ("SEM") analysis indicated that the catalyst had 15% of Cobalt (5 g) impregnated for the second time by 4 ml of aqueous solution contained 2.2 g of $Co(NO_3)_2 \times 6H_2O$. The catalyst was dried and calcinated as mentioned above. The cobalt content after twofold impregnation was 25.1% (Scanning Electronic Microscopy ("SEM") analysis). The catalyst (2.3 g) was charged in a tubular stainless steal reactor and reduced by hydrogen as in Example 1. The hydrogenation of imine was carried out under operating conditions mentioned as in Example 1. The content of cis-Sertraline in the product was 87% (Table 6).

EXAMPLE 4

Example 3 was repeated with the temperature of hydrogenation being increased to 150° C. and the feed rate of solution being increased to 40 g/hr. The content of cis-sertraline was 88.8% (Table 6).

(5° C./min), and then the temperature was maintained constant at 150° C. for 2 hours. After catalyst pre-treatment, the temperature in the reactor was decreased to 90° C., and the total pressure of hydrogen was increased to 8 atmospheres. A solution containing N-methyl-4(3,4-dichlorophenyl)-1-(–2H)-naphtalenimine (Imine) in tetrahydrofuran (THF), purchased from BioLab (99.5%), having a concentration of 30 g/L was then fed with hydrogen to the reactor. The rate of the solution feed was 250 g/h and the rate of hydrogen feed was 150 ml/mm. The content of cis -sertraline in the product of imine hydrogenation was 86%.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended embodiments and the applicable rules of law.

What is claimed is:

1. A process for preparing sertraline or an intermediate thereof comprising the step of hydrogenating an imine of the formula:

TABLE 6

The experimental results of Imine hydrogenation in a trickel bed reactor

| | | | GC analysis, % area | | | | |
|---|---|---|---|---|---|---|---|
| Examples | Catalyst | T (° C.) | Cis-SRT | Trans-SRT | DCS-1 + DCS-2 | Imine | SRT-one |
| 1 | 15% Co SA-3135 | 120 | 91.0 | 7.0 | 0.1 | Not detected | 0.3 |
| 2 | 11% Co SA-3135 | 120 | 90.4 | 7.1 | 0.1 | Not detected | 0.2 |
| 3 | 25% Co SA-3135 | 120 | 87.0 | 9.4 | 0.1 | Not detected | 0.7 |
| 4* | 25% Co SA-3135 | 150 | 88.8 | 7.0 | 0.1 | Not detected | 0.3 |

The content of imine in THF was 30 g/L, the feed of the solution was 25 g/h and the feed of hydrogen was 150 ml/min (* the feed the Imine solution was 40 g/h).

EXAMPLE 5

Resolution (±)-Sertraline hydrochloride (5 g) was dissolved in ethanol (20 mL) and KOH powder (85%) was added to the solution. The slurry was stirred at room temperature for 2.5 hrs. After stirring the solids were removed by filtration and the solution was treated with D-(–)-mandelic acid (2.66 g). Precipitation occurred and the stirring was continued for 24 hours. (+)-Sertraline-mandelate was isolated by filtration and washed with ethanol and then dried to yield 2.70 g of (+)-sertraline-mandelate.

EXAMPLE 6

The catalyst G-69 (2.9 g) was loaded into a tubular stainless steal reactor (6 mm ID and 150 mm length). In the stream of hydrogen at GHSV (gas hour space velocity) 2500h$^{-1}$, the temperature was gradually ramped to 150° C.,

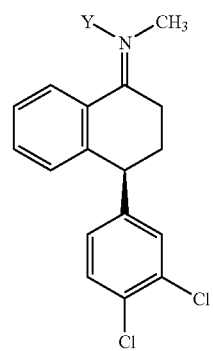

wherein Y is either absent or an oxygen atom, with a cobalt catalyst and optionally converting the hydrogenated compound to sertraline.

2. The process of claim 1, wherein the cobalt catalyst has an oxidation state of Co⁰.

3. The process of claim 1, wherein the catalyst has a cobalt content of about 10% to about 25% (wt/wt).

4. The process of claim 1, wherein the catalyst has a surface area of about 6 to about 100 m$^2$/g.

5. The process of claim 1, wherein the cobalt is fixed to a support.

6. The process of claim 5, wherein the support is alumina-silica.

7. The process of claim 1, wherein the catalyst has an average pore size of about 100 to about 300 Angstroms.

8. The process of claim 1, wherein the hydrogenating is carried out in a trickle-bed reactor.

9. The process of claim 8, wherein the hydrogenating is carried out at a temperature of about 80 to about 150° C.

10. The process of claim 8, wherein the hydrogenating is carried out at a pressure of about 5 to about 20 bar.

11. The process of claim 8, wherein hydrogenating is carried out with a hydrogen feed rate of about GHSV 25 to about 5000 per hour.

12. The process of claim 8, wherein the hydrogenating is carried out with feeding a solution of the imine in THF.

13. The process of claim 12, wherein the solution has a concentration of about 10 to about 120 grams/L.

14. The process of claim 8, wherein the hydrogenating is carried out with a weight hourly space velocity of about 5 to about 15 per hour.

15. The process of claim 8, wherein the sertraline prepared has dechlorinated side products of less than about 0.1%.

16. The process of claim 8, wherein the sertraline is prepared with a cis to trans ratio of about 6 to about 14.

17. The process of claim 16, wherein the ratio is about 12.

18. The process of claim 1, wherein the imine is a pure enantiomer.

19. The process of claim 1, further comprising increasing the ratio of (+)-cis-sertraline through selective precipitation with mandeleic acid.

20. The process of claim 1, further comprising the step of converting the sertraline to sertraline hydrochloride.

21. A process for preparing sertraline or an intermediate thereof from

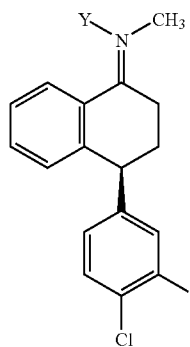

an imine having the formula:
wherein Y is either absent or an oxygen atom, comprising the step of hydrogenating the imine with a nickel containing catalyst having fixed support in a batch reactor and optionally converting the hydrogenated compound to sertraline.

22. The process of claim 21, wherein the catalyst has an oxidation state of zero.

23. The process of claim 21, wherein the catalyst has a nickel content of about 30 to about 80% wt/wt.

24. The process of claim 21, wherein the catalyst has a surface area of about 50 to about 200 m$^2$/g.

25. The process of claim 21, wherein the nickel is fixed to an alumina-silica support.

26. The process of claim 21, wherein hydrogenating is carried out at a temperature of about 65° C. to about 150° C.

27. The process of claim 26, wherein the temperature is about 120 to about 150° C.

28. The process of claim 21, wherein hydrogenating is carried out at a pressure of about 5 to about 8 bar.

29. The process of claim 28, wherein the pressure is about 8 bar.

30. The process of claim 21, wherein the imine is loaded into the reactor at about 30 g to about 125 g per liter of solvent.

31. The process of claim 21, wherein the hydrogenating is carried out in a solvent selected from the group consisting of methanol, ethanol, toluene, ethyl acetate, 1,4-dioxane and THF.

32. The process of claim 31, wherein the solvent is THF.

33. The process of claim 31, wherein the solvent is dioxane.

34. The process of claim 21, wherein a cis/trans ratio of about 7 to about 1 is obtained.

35. The process of claim 21, wherein the sertraline obtained has a DCS-compounds of less than about 0.2%.

36. The process of claim 21, further comprising the step of converting the sertraline to sertraline hydrochloride.

37. A process for preparing sertraline from sertraline-1-imine comprising the step of reducing sertraline-1-immune in a batch reactor with a Ni/Kieseilgurh catalyst.

38. The process of claim 37, wherein a ZnO$_2$ promoter is used with the catalyst.

39. A process for preparing sertraline comprising the steps of:
 a) providing a cobalt containing catalyst made up of cobalt oxide fixed on an alumina-silica support;
 b) loading the catalyst in a trickle bed reactor;
 c) reducing the cobalt oxide catalyst;
 d) feeding the reactor with hydrogen and a solution of sertraline 1-imine in THF;
 e) recovering the sertraline;
 f) optionally repeating steps (d) and (e) with a preliminary step of removing any tar on the catalyst; and
 g) optionally converting the sertraline to sertraline hydrochloride.

40. The process of claim 39, wherein reducing is carried out with a stream of hydrogen at GHSV (gas hour space velocity) 2500h$^{-1}$.

41. The process of claim 40, wherein temperature during reducing is increased to at least about 450°C., at interval of about 3–8° C. /min, and maintained constant for at least about 2 hours.

42. A process for preparing sertraline comprising hydrogenating sertraline-1-imine with a cobalt catalyst in a trickle-bed reactor fed with sertraline imine solution in THF of 30 g imine/L at weight hourly space velocity of about 12.5 h$^{-1}$, a pressure of about 8 bar and a temperature of about 120° C.

43. A process for preparing sertraline comprising hydrogenating sertraline-1-imine in solution in THF having a concentration in the range of about 10 to about 140 g/L with a nickel catalyst fixed on a support in a trickle-bed reactor, at a temperature of about 65 to about 150° C., a pressure of about 2 to about 15 bar, a WHSV of about 40 to about 120 per hour, and a hydrogen feeding range of GHSV about 50 to about 2000 per hour.

44. The process of claim 43, wherein the temperature is about 90° C., the pressure about 8 to about 10, the concentration of the imine solution at about 30 g/L, and the WHSV at about 85 per hour.

45. A process for preparing sertraline comprising hydrogenating with a nickel catalyst fixed on a support in a batch reactor sertraline-1-imine in solution in THF having a concentration in the range of about 30 to about 125 g/L, pressure of about 5 to about 8 bar, temperature range of about 65 to about 150° C.

46. The process of claim 45, wherein the pressure is about 8 bar and the temperature about 120 to about 150° C.

* * * * *